US007091320B2

(12) United States Patent
Pozzilli

(10) Patent No.: US 7,091,320 B2
(45) Date of Patent: Aug. 15, 2006

(54) PRODUCT DERIVED FROM MILK SUBSTANTIALLY FREE OF BETA CASEIN FROM NON-HUMAN MAMMALS AND RELATIVE USE

(75) Inventor: Paolo Pozzilli, Rome (IT)

(73) Assignee: Midia Limited, St. Helier-Jersey (GB)

( * ) Notice: Subject to any disclaimer, the term of this patent is extended or adjusted under 35 U.S.C. 154(b) by 0 days.

(21) Appl. No.: 10/793,111

(22) Filed: Mar. 4, 2004

(65) Prior Publication Data
US 2005/0176638 A1   Aug. 11, 2005

Related U.S. Application Data

(62) Division of application No. 09/095,639, filed on Jun. 11, 1998, now Pat. No. 6,750,203.

(30) Foreign Application Priority Data

Dec. 27, 1995  (IT) ............................. RM95A0850
Dec. 27, 1996  (WO) ...................... PCT/EP96/05846

(51) Int. Cl.
*A23J 3/10*      (2006.01)
*A61K 38/00*    (2006.01)
(52) U.S. Cl. ........................................ 530/360; 514/12
(58) Field of Classification Search ................ 530/360; 514/12
See application file for complete search history.

(56) References Cited

U.S. PATENT DOCUMENTS 6,451,368 B1 * 9/2002 Elliott et al. ................. 426/580

FOREIGN PATENT DOCUMENTS

WO    WO 9304172 A2 *  3/1993

OTHER PUBLICATIONS

Lönnerdal et al. Cloning and Sequencing of a cDNA Encoding Human Milk Beta-Casein. FEBS Letters. Aug. 1990. vol. 269, No. 1, pp. 153-156.*
209 amino acid sequence of Beta-casein A1 variant from Bovine taurus: Accession code: 1314242A.*
224 amino acid sequence of Beta-casein A2 variant from Bovine taurus: Accession code: NP_851351..*
226 amino acid sequence of Beta-casein from Homo sapiens: Accession code: NP_001882.*
Greiner. History of Breastfeeding. The Nursing Mothers' Asociation of Australia Christmast Newletter. 1998. vol. 34, No. 6, pp. 4-5.*
Akerblom et al. Dietary manipulation of beta cell autoimmunity in infants at increased risk to type 1 diabetes: a pilot study. Diabetologia. 2005. vol. 48, pp. 829-837.*
Healthcare Professional Resource Center: Enfamil, Nutramigen, LIPIL. Hypoallergenic Protein Hydrolysate Formula.   www.meadjohnson.com/professional/products/nutramigenlipil.html.*
H.K. Akerblom, "The Case for Elimination of Cow's Milk in Early Infancy in the Prevention of Type 1 Diabetes: The Finnish Experience" Diabetes/Metabolism Reviews, vol. 9, No. 4, pp. 269-278 (1993) by John Wiley & Sons, Ltd., Helsinki, Finland.
Denis Daneman, et al "Dietary Triggers of Insulin-Dependent Diabetes in the BB Rat" Diabetes Research pp. 93-97 (1987) Teviot-Kimpton Publications, Toronto, Canada.
R. B. Elliot, et al "Dietary Triggers of Diabetes in the NOD Mouse" Frontiers in diabetes research. Ed E. Shafrir. III 4 pp. 195-197. (1990).
R.B. Elliot, et al Dietary Protein: a Trigger of Insulin-Dependent Diabetes in the BB Rat? Research Institute Diabetologia Springer-Verlag (1984) vol. 26: pp. 297-299.
R.B. Elliot, et al "Dietary Prevention of Diabetes in the Non-obese Diabetic Mouse" Diabetologia Springer-Verlag (1988) vol. 31: pp. 62-64.
Julio M. Martin, et al "Milk Proteins in the Etiology of Insulin-Dependent Diabetes Mellitus (IDDM)" Annals of Medicine vol. 23: pp. 447-452 (1991).
S. Reddy, et al "A Combined Casein-Free-Nicotinamide Diet Prevents Diabetes In the NOD Mouse With Minimum Insulities" Diabetes Research and Clinical Practice vol. 29 pp. 83-92 (1995).
Suvi M. Virtanen, et al "Early Introduction of Dairy Products Associated with Increased Of Risk of IDDM in Finnish Children" Diabetes vol. 42 pp. 1786-1790 (1993).
Luis Castano, et al "Type I Diabetes: A Chronic Autoimmune Disease of Human, Mouse, and Rat" Annual Reviews Immunol., vol. 8 pp. 647-679 (1990).
Hertzel C. Gerstein "Cow's Milk Exposure and Type I Diabetes Mellitus" Diabetes Care, vol. 17 No. 1, pp. 13-19 (1994).
Faser W Scott Cow Milk and insulin-dependent diabetes mellitus: is there a relationship? American Society for Clinical Nutrition, vol. 51 pp. 489-491 (1990).
G. Dahlquist, et al "An increased level of antibodies to beta-lactoglobulin is a risk determinant for early onset Type I diabetes mellitus independent of islet cell and antibodies and early introduction of cow's milk" Diabetologia, vol. 35, pp. 980-984 (1992).
Knul Dahl-Jorgensen, et al "Relationship Between Cow's Milk Consumption and Incidence of IDDM in Childhood" Diabetes Care vol. 14 No. 11, pp. 1081-1083 (1991).

(Continued)

*Primary Examiner*—Karen Cochrane Carlson
*Assistant Examiner*—Suzanne M. Noakes
(74) *Attorney, Agent, or Firm*—James V. Costigan; Hedman & Costigan

(57) ABSTRACT

The present invention is related to a product derived from milk, substantially free of beta casein from non-human mammals. The invention is also related to the use of such a product especially in relation to diet, more particularly for early infancy, in the prevention of insulin-dependent diabets.

1 Claim, 3 Drawing Sheets

OTHER PUBLICATIONS

R.B. Elliot, et al "Prevention of Delay of Type I (Insulin-dependent) diabetes mellitus in children using nicotinamide" Diabetologia, vol. 34 pp. 362-365 (1996).

Pediatr. Adolesc. Endocrinol. Basel, Karger 1993. vool.23, pp. 97-104.

Diabetologia 1993:36: EASA News Section pp. 51-53.

* cited by examiner

PRODUCT DERIVED FROM MILK SUBSTANTIALLY FREE OF BETA CASEIN FROM NON-HUMAN MAMMALS AND RELATIVE USE

This application is a division of Ser. No. 09/095,639, filed Jun. 11, 1998 now U.S. Pat. No. 6,750,203 which claims priority from Italian Appln. Serial No. RM 95A000850, filed Dec. 27, 1995 and PCT/EP96/05846 filed Dec. 27, 1996.

FIELD OF THE INVENTION

The present invention is related to a product derived from milk substantially free of beta casein from non-human mammals. The invention is also related to the use of such a product especially in terms of its application in relation to diet, particularly for early infancy, in the prevention of insulin-dependent diabetes.

PRIOR ART

The technique of obtaining products, especially food products, for early infancy is well-known, starting from non-human milk, such as cow's, sheep and goat's milk. The basic component of milk is characterized by casein, which in basic terminology represents a group of proteins obtainable by milk precipitation at acid pH and up to room temperature, specifically pH 4.6 and 20° C. Caseins represent approximately 80% of total cow's milk proteins and 40% p/v human milk. Casein can be sub-divided into three main groups: alpha, beta and kappa. There is also a fourth group, represented by gamma casein, which is derived from beta casein following the removal of the first twenty-two amino acids. Therefore, for the present invention, gamma casein will be considered as part of beta casein.

Beta casein represents approximately 70% p/v of all casein present in human milk, whereas in cow's milk, it represents approximatly 25% p/v. Of bovine beta casein, several genetic variants are known and have been characterized, including A1, A2, A3, B, C, D and E. For the industrial production of milk, mainly the genetic variant of milk A1 has been favored to increase the amount of milk produced. This variant, which contains more proteins than others, has been obtained from various selected animals, in particular cows. By gene data sequencing analysis, the amino acid sequence in position 63–68 has been identified for cow's beta casein A1, corresponding to the 54–59 sequence of human beta casein. A similar situation has been discovered with regard to the variant A2. Both variants A1 and A2 of beta casein also show sequence homology in that region (at least 90 percent) with a specific protein of insulin-producing cells in the pancreas (GLUT2). According to the inventor, the sequence 63–68 of A1 and A2 beta casein and, more generally, the analogue sequences of other types of casein, such as A1, A2, A3, B, C, D and E, elicit an immune response via production of anti beta casein antibodies and lymphocytes which recognize such sequences. For newborns and infants in the first months of life, a diet containing these immunogenic caseins might induce a specific immune response to GLUT2 in the insulin-producing cells of the pancreas by a mechanism of molecular mimicry with the homologous sequence of beta casein. On the basis of such a hypothesis, a study has been carried out, aiming to obtain bovine milk products substantially free of non-human beta casein and, more specifically, beta casein containing products from non-human mammals that do not result to be immunogenic with respect to the GLUT2 protein because of absence of such sequence homology.

SUMMARY OF THE INVENTION

The present invention is related to a product derived from milk or milk itself, substantially free of non-human beta casein with immunogenic characteristic as specified in prior art.

Another object of the invention is a milk-derived product or milk itself comprising al least one beta casein modified from non-human mammals without the immunogenic characteristic mentioned above. Another object of the invention is the use of such a product, in relation to diet.

Another object of the invention is the use of a product from milk or milk itself, substantially free of non-human mammals beta casein in order to obtain a food for the early infant diet for the prevention of insulin-dependent diabetes.

Further objects of the invention will be evident from the detailed description of the invention

DETAILED DESCRIPTION OF THE INVENTION

In the attached description the amino acid sequences of importance according to the invention will be underlined. The word "substantially free" will indicate the presence of the substance (s) to which it refers in amounts ranging between 0 to 10% b.w.

The amino acid sequence of interest for the present invention is described hereafter. As mentioned above, according to the inventor there is a correlation between exposure to cow's milk and the development of insulin-dependent diabetes due to molecular mimicry between the amino acid sequences of beta casein A1 and A2 and a specific sequence of the GLUT2 protein found in the insulin-producing cells. Such a sequence has been identified as follows:

Pro-Gly-Pro-Ile-His-Asn (where the underlined sequence is SEQ ID NO:1) for the A1 beta casein inserted in the larger fragment: Ser-Leu-Val-Tyr-Pro-Phe-Pro-Gly-Pro-Ile-His-Asn (SEQ ID NO:3).

As already stated, such a sequences is also present in gamma casein. Other sequences corresponding to immunogenic peptides of beta casein which are different from those mentioned above are given as examples. Cow's beta casein A2 from bos taurus (63–68), Pro-Gly-Pro-Ile-Pro-Asn (where the underlined sequence is SEQ ID NO:2) inserted in the larger fragment: Ser-Leu-Val-Tyr-Pro-Phe-Pro-Gly-Pro-Ile-Pro-Asn (SEQ ID NO:4)

Beta casein from bos indicus (63–68) Pro-Gly-Pro-Ile-Pro-Asn (underlined sequence SEQ ID NO:2).

In comparison, human beta casein has the following sequence (48–59): Ser-Leu-Val-Tyr-Pro-Phe-Val-Glu-Pro-Ile-Pro-Tyr (SEQ ID NO:6). The peptide fraction relevant to the present invention has been identified as (54–59): Val-Glu-Pro-Ile-Pro-Tyr (where the underlined sequence is SEQ ID NO:5). The peptide sequences of GLUT2, the glucose transporter inside insulin-producing beta cells in the pancreas, are the following:

(409–420) Ser-Phe-Phe-Glu-Ile-Gly-Pro-Gly-Pro-Ile-Pro-Trp (412–423) Glu-Ile-Gly-Pro-Gly-Pro-Ile-Pro-Trp-Phe-Met-Val (414–425) Gly-Pro-Gly-Pro-Ile-Pro-Trp-Phe-Met-Val-Ala-Glu

The inventor suggests that the sequence of A1, B and C beta casein and gamma casein, Pro-Gly-Pro-Ile-His (SEQ ID NO:1), and the larger fragments containing it, such as the sequences of beta casein A2, A3 and E, Pro-Gly-Pro-Ile-Pro (SEQ ID NO:2), are responsible for the induction of an immune response towards beta casein which, by cross reactivity, would be directed towards the homologous sequence of GLUT2, causing damage to the cells that produce insulin.

Therefore to produce a milk or in general, food product comprising non-immunogenic beta casein for administration in diets, particularly to newborns and in early infancy, would be a preventive approach against insulin dependent diabetes.

All caseins which do not contain the sequence Pro-Gly-Pro-Ile-His (SEQ ID NO:1) or Pro-Gly-Pro-Ile-Pro (SEQ ID NO:2) are not considered pathogenic and, therefore, can be used to produce a dietary product in accordance with the present invention:

some or all amino acids present in the above sequence are modified;

beta casein does not contain such a sequence (e.g., it has been removed)

beta casein is modified in that such a sequence is substituted with a sequence of human beta casein;

All modifications can be made by applying the well-known technique of genetic engineering and the classic biological technique of cross-selection, as described in patent WO 93/04171.

The milk obtained, comprising casein modified as stated above, can be administered as such or can be treated with known methods, as the casein(s) involved can be separated and used to produce food and pharmaceutical products.

In particular, the products including such casein can be used for adiministration in early infancy and later on as a diet for the prevention of insulin-dependent diabetes.

It is preferred that, in products according to the present invention, concentrations of A1 and/or A2 and/or other immunogenic beta caseins, in particular those with the sequence Pro-Gly-Pro-Ile-His (SEQ ID NO:1) or Pro-Gly-Ile-Pro (SEQ ID NO:2), do not represent more than 10% b.w. of th final product.

The food products of the invention can be, for instance, pasta, milk and milk-derived products and proteins, such as those added to food, all of which are already in the market-place, the modification being the substitution of the immunogenic caseins with the caseins of the present invention.

Also part of the present invention are vegetable and/or synthetic proteins, such as those derived from soya. According to the teaching of the invention, it is possible to produce a pharmaceutical or food product, especially for early infancy, substantially free of beta casein, with the amino acid sequence Pro-Gly-Pro-Ile-His (SEQ ID NO:1) or Pro-Gly-Pro-Ile-Pro (SEQ ID NO:2), or where such sequences are less than 10% of the final weight of the product. It is also possible to produce a food product or a milk according to the following alternatives:

where the beta casein is lower than 10% b.w. or the beta casein comprising the amino acid sequence Gly-Pro-Ile-His (SEQ ID NO:7) or Gly-Pro-Ile-Pro (SEQ ID NO:8) is lower than 10% by w.

substantially free of beta casein comprising the amino acid sequence Gly-Pro-Ile-His (SEQ ID NO:7) or Gly-Pro-Ile-Pro (SEQ ID NO:8) and integrated with peptides derived from the hydrolysis of animal, vegetable and/or synthetic proteins, and lacking these above sequences and mixtures thereof (FR 86-00325, WO 94/06306, WO p (02539));

where the beta casein comprising the amino acid sequence Gly-Pro-Ile-His (SEQ ID NO:7) or Gly-Pro-Ile-Pro (SEQ ID NO:8) is lower than 10% b.w. and integrated with peptides coming from hydrolisis of animal and/or vegetal and/or synthetic proteins lacking such sequences and mixtures thereof;

where the beta casein is lacking the amino acid sequence Gly-Pro-Ile-His (SEQ ID NO:7) or Gly-Pro-Ile-Pro (SEQ ID NO:8) in that it has been obtained from animal species genetically not producing proteins with such sequences;

milk naturally lacking beta casein, produced by genetically modified animals according to patent WO 93/04171;

milk comprising human beta casein obtained from genetically manipulated microorganisms or animals, such as those described in the above mentioned patent.

The protein fractions can be derived from chemical-physical treatments of milk and from lyophylized casein, for instance by differential solubility, liquid-liquid extraction, membrane separation, chromatographic separation, as described in patents FR 86-00325 and WO92/00017.

The integrations can be carried out by using recombinant beta casein produced with one of the well-known cloning methods, using yeat, bacteria, funghi or transgenic animals, such as those described in patent WO 93/04171.

A process for removing beta casein from milk is the chromatographic process, as described below.

By means of such a process the beta casein is separated, starting from acid casein, and by means of chromatography in two steps, the remaining fractions of alpha and kappa casein will be obtained.

The process can be optimized using the knowledge already available in the field. Such a process includes the use, as basic phase, of a resin of ionic exchange, for example Sepharose® from Pharmacia, with the concentration also in columns. The mobile phase is constituted by Buffer A:

Sodium acetate with concentration not less than 10 mM;
urea at concentration not less than 2M;
pH between 5 and 6.

The acid casein can be dissolved in Buffer A at pH not less than 6, with the addition of a specific reducing agent, DTT, (Ditiotreeitol). The mixture should be left under for 24 hours, brought to pH between 5 and 6 and placed in columns. The beta casein fraction does not interact with the resin and is eluted 0M NaCl. It is not necessary, therefore, to carry out stages of increasing ionic concentration, considering that the process at hand merely involves a simple separation of beta casein from the other fractions, which will be collected in isocratic by eluting with buffer B:

Sodium acetate at concentration no less than 10 mM;
urea at concentration no less than 2M;
0.8 M NaCl;
pH between 5 and 6.

The fractions are later dialfiltrated to eliminate urea and other salts; after concentration, caseins are collected by acid precipitation and the obtained wet product is lyophilized.

Figure 1:
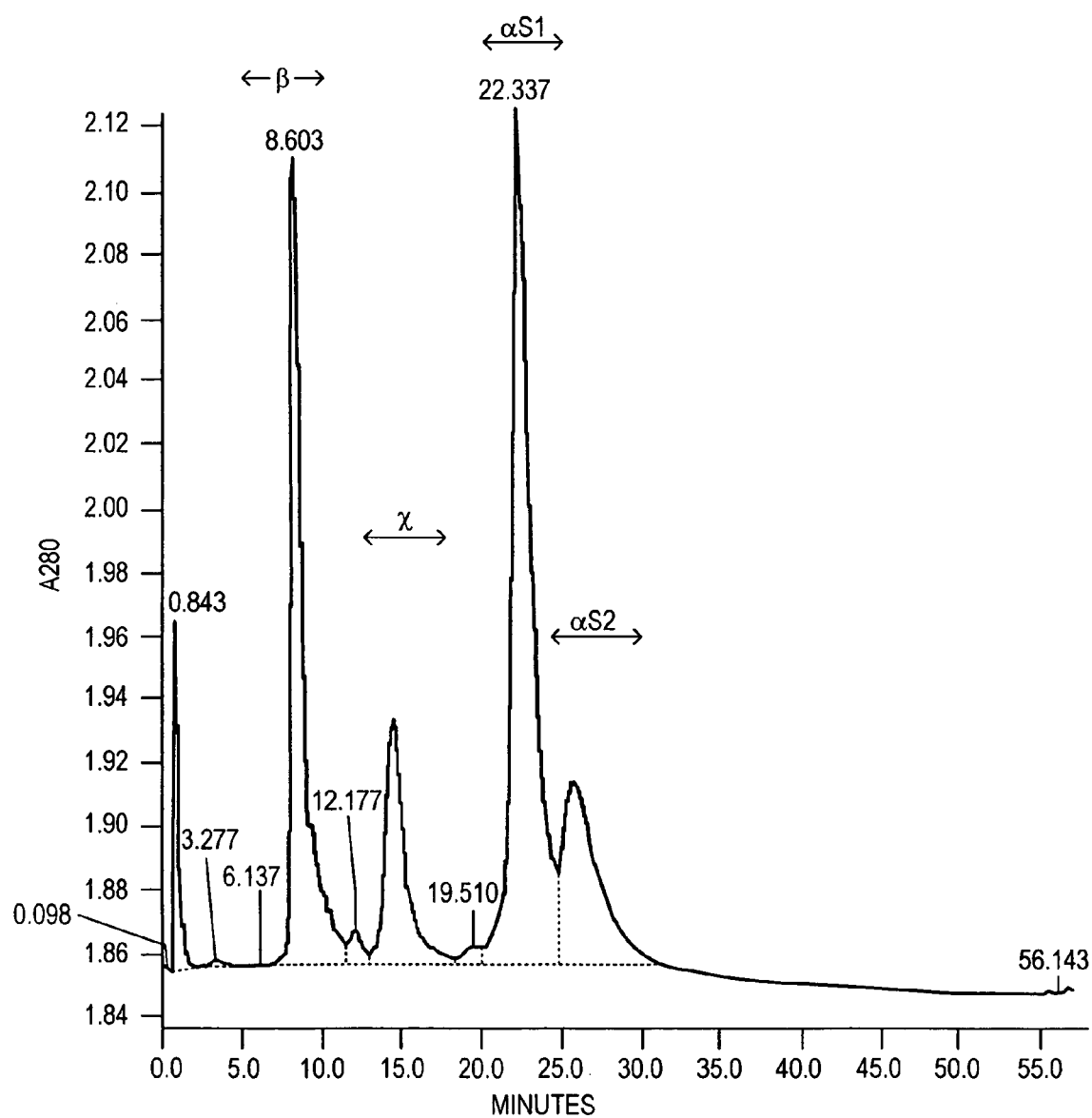
FIG. 1 is the chromatogram relating to the initial load of Example 1.

The following examples are to be considered as illustrative of such a technique, therefore they should be not considered a limitation of the gist of the present invention.

EXAMPLE 1

Separation of Beta Casein from Acid Casein and Collection of the Remaining Alpha and Kappa Casein Fractions.

Preparation

−200 g acid casein +3000 ml Buffer C: 20 mM sodium acetate. 4M urea, 10 mM (ditioltreeitol) DTT pH 7.

Casein should be slowly dissolved in the buffer, keeping pH 7 with 2M NaOH at each addition.

Leave under stirring at 5° C. for approximately 12 hours.
Filtrate the solution in pre-filter Millex AP-50 (Millipore)
Wash the prefilter with 1000 ml of Buffer C and collect.
Bring the load (4000 ml) to pH 5.5 with HCl 6M and adjust the ionic strength (2.2 mS) to 4.5 mS.

| Preparational Chromatography | |
|---|---|
| FPLC | Waters 600 Controller |
| Revelator: | Perkin Elmer UV/VIS Spectrophotometer Lambda 3B 280 nm |
| Column: | XK 50 Pharmacia (maximum pressure 3 bar) 0 5 cm, height 100 cm |
| Resin: | S-Sepharose Pharmacia height 85 cm, volume 1670 ml |
| Eluents: | Buffer A  Sodium acetate 20 mM<br>Urea 4 M<br>pH 5.5, ionic strength 1.5 mS |
|  | Buffer B  Sodium acetate 20 mM<br>Urea 4 M<br>pH 5.5<br>Sodium chloride 1 M ionic strength 57.1 mS |

All buffers are filtrated by using a Millex pre-filter AP 50 bound in series with filter 0.45 μm Millipak 20 (Millipore).
Temperature: Room temperature
Conditioning: ≈8000 ml
  Buffer A: 97% Buffer B: 3% ionic strength mix:
  4.5 mS
  Flow: 30 ml/min P=42 PSI
  Time: 4 hours, 25 minutes
Loading: 200 g acid casein dissolved in Buffer C (total volume 4000 ml)
  Flow: 20 ml/min P=50 PSI
  Time: 3 hours, 20 minutes
Elution: First Stage (isocratic)≈8000 ml
  Buffer A:97% Buffer B:3%
  Flow: 30 ml/min P=42 PSI
  Time: 4 hours, 25 minutes
  Second Stage (isocratic) 9000 ml
  Buffer A:20% Buffer B:80%
  Flow: 30 ml/min P=42 PSI
  Time: 5 hours

EXAMPLE 2

Control Test

Figure 2:
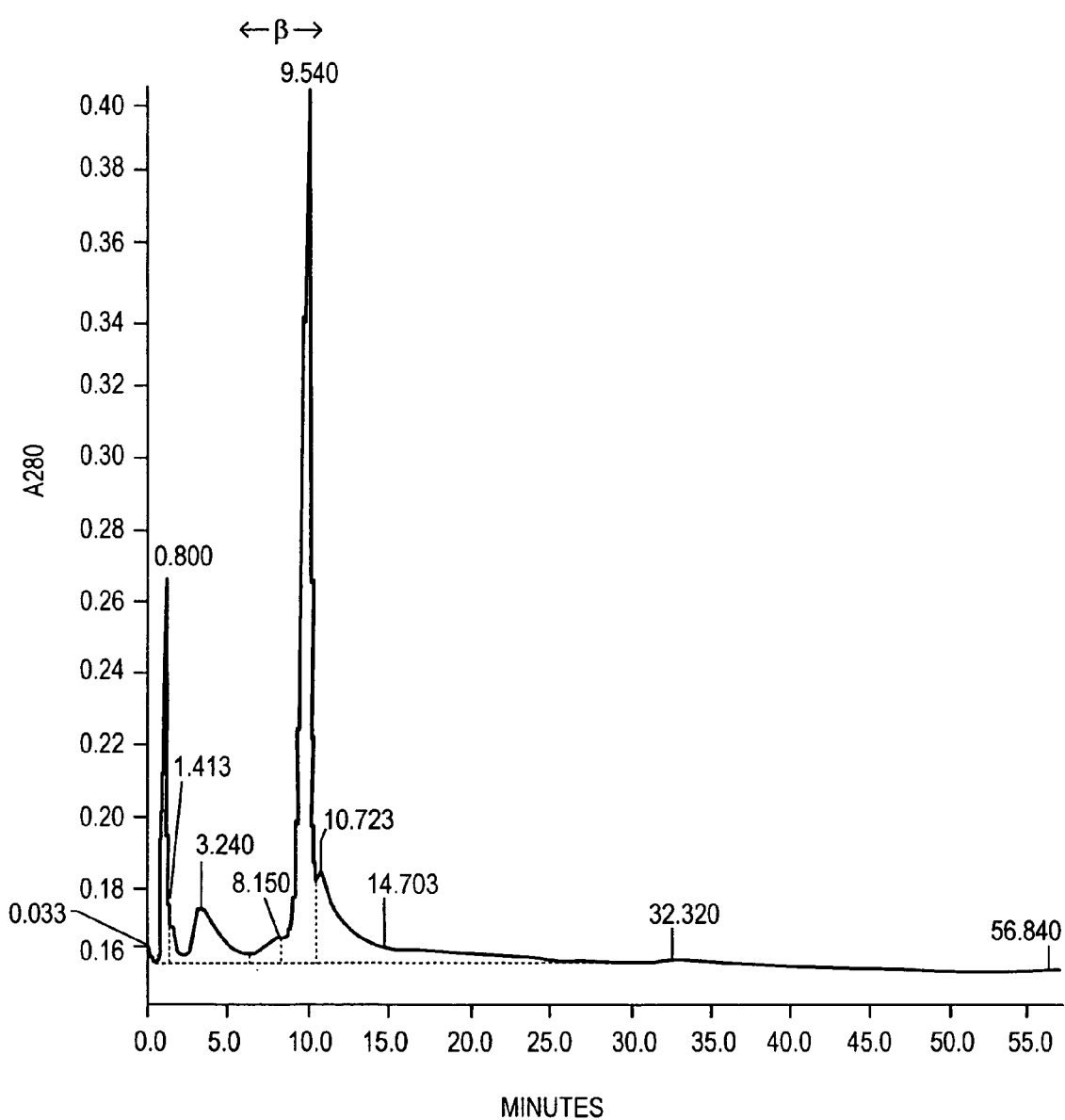
FIG. 2 illustrates a chromatographic peack relating to the beta casein.
Figure 3:
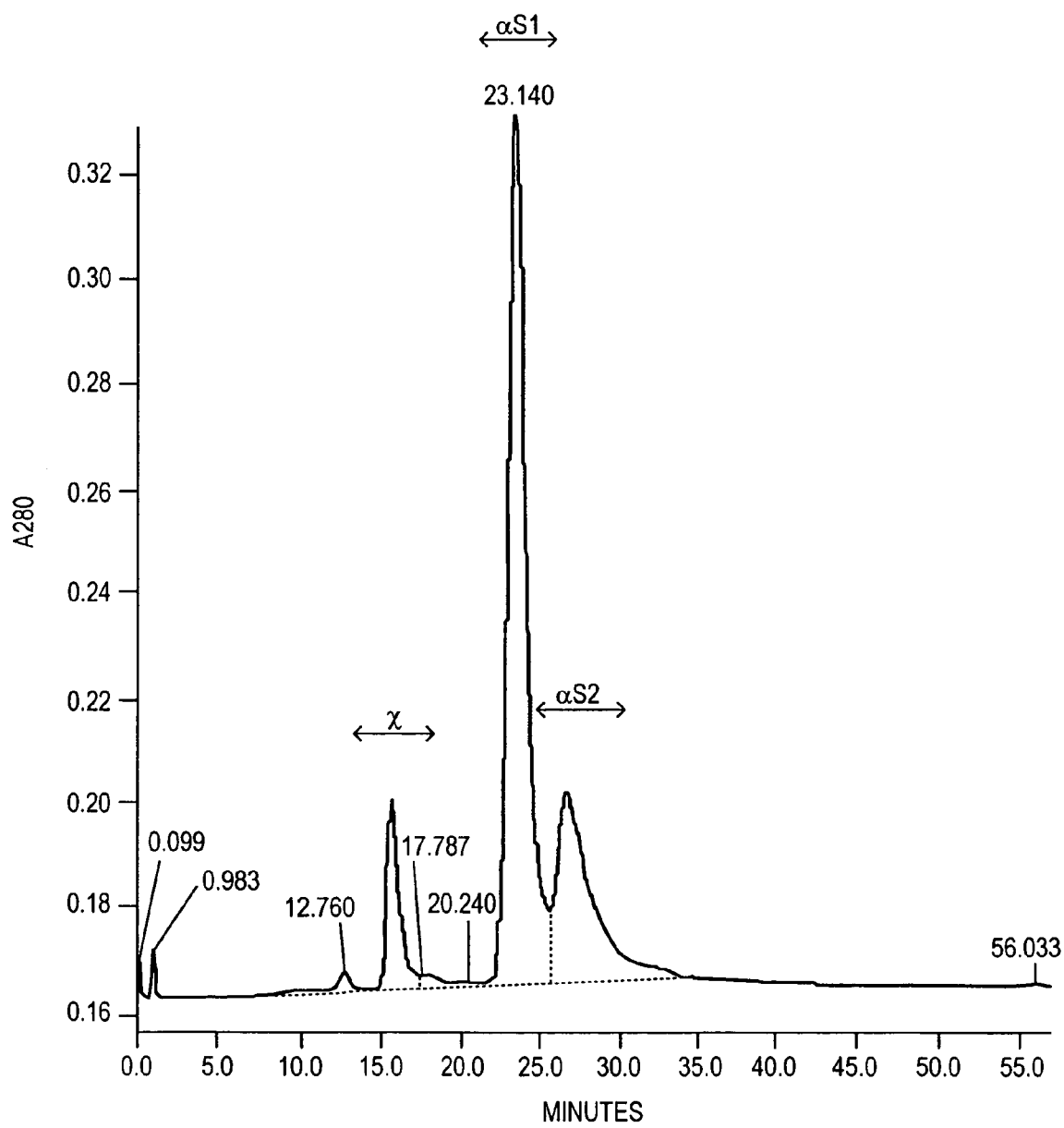
FIG. 3 refers to the absence of the beta casein in the chromatogram.

An amount of the product from example 1 is tested by chromatography to evaluate the absence of beta casein in the isocratic of the second stage. Such absence is confirmed as demonstrated by the chromatogram of FIG. 3. By comparison in FIG. 1, the chromatogram relating to the initial load is illustrated, whereas in FIG. 2 the peak relating to the presence of beta casein only derived from the elution of the first stage is represented.

| Analytic chromatography | | | |
|---|---|---|---|
| HPLC | Perkin Elmer Biocompatible Binary Pump 250 | | |
| Revelator: | Perkin Elmer LC95 280 nm | | |
| Column: | Mono S HR 5/5 Pharmacia | | |
| Loop: | 100 μl | | |
| Eluents: | Buffer A* | Sodium acetate 20 mM<br>Urea 6 M<br>pH 5 | |
|  | Buffer B* | Sodium acetate 20 mM<br>Urea 6 M<br>Sodium chloride 1 M<br>pH 5 | |
| Temperature | Room temperature | | |
| Flow: | 1 ml/min | | |
| Conditioning: | 8'00" | Buffer A* 100% | Buffer B* 0% |
| Elution: | gradient<br>5'00" | Buffer B* 50% | Buffer B* 50%<br>(increase of B* 1% min) |
| isocratic | 2'00" | Buffer A* 50% | Buffer B* 50% |
| isocratic | 5'00" | Buffer A* 0% | Buffer * 100% |

EXAMPLE 3

The Product of Example 1 has been purified from urea by the following method of diafiltration.

Ultrafiltration S.G.I.
Cellulose membrane S-10 10.000 Da Amicon
Buffer of dialysis: demineralized water
  sodium acetate 10 mM ph?7
  ionic strength 0.8 mS
  total volume 250 l (5 washes)
Permeate flow: 32÷37 l/h
Temperature: 10° C.
Product concentration 50 l up to 20 l The product has been tested to verify the absence of urea as follows:

| Urea Test | | |
|---|---|---|
| UV method (Boehringer Mannheim) | | |
| Spectrophotometer: Lambda 3B 340 nm (Perkin Elmer) | | |
| Reagents | Blank | Sample |
| Solution 1 | 1.00 ml | 1.00 ml |
| Sample solution | — | 0.10 ml |
| Solution 2 | 0.02 ml | 0.02 ml |
| Bidistilled water | 2.00 ml | 1.90 ml |
| Incubate 5' at 20–25° C.; read the absorbance (A1) | | |
| Solution 3 | 0.02 ml | 0.02 ml |
| Incubate 20' at 20–25° C.; read the absorbance (A2) | | |

Solution 1 = Triethanolamin buffer, pH 8.2 oxoglutarate, NADH
Solution 2 = Urase
Solution 3 = Dehydrogenase glutamate The lyophilization is carried out on the product free of urea, by using a Christ model Beta 1–16 equipment.

The invention claimed is:

1. A method for the reducing the occurrence of insulin-dependent diabetes comprising the step of administering to newborns and infants, who will exhibit in response to feeding of non-human beta casein, an immune response which will cause insulin-dependent diabetes, an infant formula derived from non-human milk, said infant formula being substantially free of non-human beta caseins that exhibit molecular mimicry with protein GLUT 2.

* * * * *

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 1:

Pro Gly Pro Ile His
1               5

(2) INFORMATION FOR SEQ ID NO: 2:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

Pro Gly Pro Ile Pro
1               5

(2) INFORMATION FOR SEQ ID NO: 3:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Ser Leu Val Tyr Pro Phe Pro Gly Pro Ile His Asn
1               5                   10

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Ser Leu Val Tyr Pro Phe Pro Gly Pro Ile Pro Asn
1               5                   10

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Val Glu Pro Ile Pro
1               5

(2) INFORMATION FOR SEQ ID NO: 6:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Ser Leu Val Tyr Pro Phe Val Glu Pro Ile Pro Tyr
1               5                   10

(2) INFORMATION FOR SEQ ID NO: 7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Gly Pro Ile His
1

(2) INFORMATION FOR SEQ ID NO: 8:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

Gly Pro Ile Pro
1